(12) United States Patent
Ukrayinecz et al.

(10) Patent No.: US 6,340,692 B1
(45) Date of Patent: Jan. 22, 2002

(54) INJECTABLE ANESTHETIC

(76) Inventors: Ihor Vasiliovych Ukrayinecz, P/O Bolshaia Danilovka, Mzhk International, 40 apt. 11, Kharkiv 62442; Petro Avsentiyovych Bezuhliy, Prospect 50-let VlKSM, 53 apt. 251, Kharkiv 61120, both of (UA)

( * ) Notice: Subject to any disclaimer, the term of this patent is extended or adjusted under 35 U.S.C. 154(b) by 0 days.

(21) Appl. No.: 09/612,656

(22) Filed: Jul. 7, 2000

Related U.S. Application Data

(60) Provisional application No. 60/142,990, filed on Jul. 8, 1999.

(51) Int. Cl.[7] ................................................ A61K 31/47
(52) U.S. Cl. ........................................................ 514/312
(58) Field of Search .......................................... 514/312

(56) References Cited

PUBLICATIONS

Chem. Abstracts AN#1995:456530, Ukarinets, et al., Khim. Geterotsikl. Soedin (10), 1400–5, 1994.*
Chem. Abstracts AN#115:49362 Ukrainets, et al.., Farm. ZH (2), 78–80, 1991.*

* cited by examiner

*Primary Examiner*—Raymond Henley, III
(74) *Attorney, Agent, or Firm*—Joseph Stecewycz

(57) ABSTRACT

An injectable anesthetic composition is disclosed comprising a solution of chinoxicaine (hydrochloride diethylaminoethylamide 1-propyl-2 oxy-4-hydroxyquinolin-3-carbonic acid) in a pharmaceutically acceptable liquid vehicle.

4 Claims, No Drawings

INJECTABLE ANESTHETIC

CROSS REFERENCE TO RELATED APPLICATION

The present Application is related to Provisional Application serial no. 60/142,990 filed on Jul. 8, 1999.

BACKGROUND OF THE INVENTION

Field of the Invention

The present invention relates in general to anesthetic compositions and, in particular, to an injectable anesthetic composition comprising a specified mixture of chinoxicaine.

SUMMARY OF THE INVENTION

The disclosed invention includes an injectable anesthetic composition comprising a solution of chinoxicaine (hydrochloride diethylaminoethylamide 1-propyl-2 oxy-4-hydroxyquinolin-3-carbonic acid) in a pharmaceutically acceptable liquid vehicle. Other objects of the present invention will in part be obvious and will in part appear hereinafter. The invention accordingly comprises the processes and products, together with their steps, elements and interrelationships, that are exemplified in the following disclosure, the scope of which will be indicated in the appended claims.

DETAILED DESCRIPTION OF THE INVENTION

The following detailed description of the present invention is not to be taken in a limiting sense but is intended to illustrate the general principles of the invention. The scope of the invention is best defined by the appended claims.

Description of the Invention

The chemical composition of the preferred embodiment is hydrochloride diethylaminoethylamide 1-propyl-2 oxy-4-hydroxyquinolin-3 -carbonic acid, denoted herein as chinoxicaine. As disclosed herein, chinoxicaine has the following formulation:

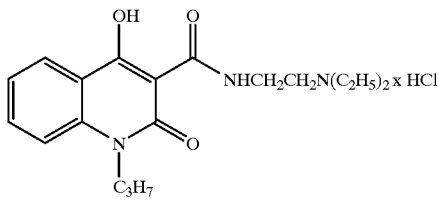

The preferred composition of chinoxicaine can be prepared by means of a process which includes the steps of:
1. Acylation of ether N-propylantranyl acid ethoxymalonilchloride in a hydroorganic dual-phased system in the presence of sodium carbonate as an acceptor of hydrochloride.
2. Transformation of the reactive mixture by way of a water solution of potassium hydroxide.
3. Separation of 1-propyl-2 oxy-3-carbotoxy-4-hydroxyquinolin in the form of potassium salt.
4. Amidifying with diethylaminethylamine in an alcohol environment in the presence of acetic acid.
5. Transformation of the resultant amide into hydrochloride.

The disclosed composition is distinguishable by the fact that diethylaminoethylamide 1-propyl-2-oxy-hydroxyquinolin-3-carbonic acid is transferred into hydrochloride in a water environment by virtue of the water solution of HCl.

Infiltration Anesthesia

Chinoxicaine provides for long and deep infiltration anesthesia, including epidural and peridermal anesthesia In way of example, a 0.5% solution of chinoxicaine can be as much as 2.5 times as effective as Lidocaine or Azacaine in long infiltration applications. In rabbits, chinoxicaine epidural and peridermal anesthesia induced a long and deep anesthesia for about 270 minutes.

The pharmacological activity of chinoxicaine has been evaluated using the characteristics of: i) strength of anesthesia, ii) latent period, and iii) duration of anesthesia. A study of infiltration anesthesia was conducted according to the Beulbring-Wade method on male guinea pigs. The median effective concentration ($EC_{50}$) was 0.1%. Latent period was about 1.5 minutes. The duration of deep anesthesia was: i) 25 minutes for the 0.1% solution, ii) 140.5 minutes for a 0.25% solution, iii) 310.8 minutes for a 0.5% solution, and iv) 313.8 minutes for a 1.0% solution. On the basis of specific pharmacological activity data, described in greater detail below, chinoxicaine is preferably provided as either a 0.25% or 0.5% solution in 250 mL bottles for use in infiltration anesthesia, and as a 1.0% or 2.0% solution in 5 mL ampoules for conduction and epidural anesthesia. In alternative embodiments, the anesthesia solution includes a 0.9% solution of sodium chloride.

A study of sciatic nerve conduction anesthesia in rats was conducted in accordance with the Camaugis-Tekman method. Prior to injection of the anesthesia, the rat motor activity was evaluated by applying a compression to the animal's feet. Then, a 0.2 mL volume of chinoxicaine solution was injected into the sciatic nerve area of the pronated lower extremity. With the application of a subsequent compression to the its feet, the animal's reaction was evaluated by observing if the animal pulled apart its toes in a 'fan-shaped' manner when suspended by its tail. It was determined that both 1.0% and 2.0% concentrations of chinoxicaine solutions produced fast, deep, and prolonged anesthesia. The anesthesia reached fill extent within 2.0±0.3 minutes, with either concentration. The duration of the anesthesia was observed to be 138.0±8.9 minutes at the 1.0% concentration, and 205.0±12.6 minutes at the 2.0% concentration.

A study of epidural anesthesia was conducted on male chinchilla rabbits. The epidural puncture was made in the area of the third and fourth lumbar vertebrae by means of a Tuohi-Peridur needle. A 2.0% solution of chinoxicaine was injected into the epidural area in a volume determined in accordance with the following formula:

$$V = 0.7 \, \frac{\text{Body weight (in kg)}}{2}$$

The results obtained showed that chinoxicaine elicits a deep and prolonged anesthesia within 5.0 minutes of injection, with an effective duration of at least 200 minutes, as compared with a duration of about 100 minutes for Lidocaine.

On the basis of test results, chinoxicaine demonstrated a two-fold increase in activity as compared to Lidocaine for either infiltration or epidural anesthesia, and a comparable increase over Trimecaine for either infiltration or conduction anesthesia.

Conduction Anesthesia

It has also been shown that the disclosed composition is suitable for conduction anesthesia, where some models indicate the average duration of deep conduction for a 1.0% solution of chinoxicaine anesthesia to be 3 to 5.5 hours. In conduction applications, a 0.5% solution of chinoxicaine exhibits an effective duration of as much as twice that of Trimecaine or Lidocaine.

A study of conduction anesthesia was carried out on white non-breeding rats weighing 180 to 220 grams. The anesthetic solution was injected under the tail skin on four sides in a 1.0 mL volume at concentrations ranging from 0.1% to 1.0%. Duration of the anesthetic solution was $120.3 \pm 7.1$ minutes for the 0.1% concentration, $300.5 \pm 15.5$ minutes for a 0.25% concentration, $306.0 \pm 16.2$ minutes for a 0.5% concentration, and $320.0 \pm 13.1$ minutes for the 1.0% concentration.

Moreover, because the disclosed composition provides for antimicrobial action against saprophytic and aerobic gram-positive and gram-negative bacterial flora, and exhibits fungicidal action against pathogenic fungi strains, use of chinoxicaine is particularly suitable in surgical drainage of pus abuss, stomatology, and dentistry, thus reducing the incidence of post-operative complications.

Having thus described the invention with reference to the several embodiments, it will be understood that other modifications and variations may occur to those skilled in the art without departing from the spirit and the scope of the invention. Accordingly, the various changes in form and in detail which may be made are intended to fall within the scope of the appended claims.

What is claimed is:

1. A method of inducing anesthesia in a mammal, said method comprising the step of administering intravenously to the mammal a composition of chinoxicaine sufficient to produce infiltration anesthesia.

2. The method of claim 1 wherein said composition of chinoxicaine comprises a solution of chinoxicaine in a pharmaceutically acceptable liquid vehicle.

3. The method of claim 2 wherein said composition of chinoxicaine comprises a solution of between 0.1 percent and 2.0 percent.

4. The method of claim 1 wherein said composition of chinoxicaine comprises approximately a 0.9 percent solution of sodium chloride.

\* \* \* \* \*